United States Patent [19]

Wang

[11] Patent Number: 4,475,904
[45] Date of Patent: Oct. 9, 1984

[54] FAST RESPONSE VACUUM ASPIRATION COLLECTION SYSTEM

[75] Inventor: Carl C. T. Wang, San Leandro, Calif.

[73] Assignee: Medical Instrument Dev. Labs., Inc., San Leandro, Calif.

[21] Appl. No.: 454,470

[22] Filed: Dec. 29, 1982

[51] Int. Cl.³ .............................................. A61M 1/00
[52] U.S. Cl. ..................................... 604/119; 604/323
[58] Field of Search ....................... 604/27, 35, 48, 65, 604/93, 118, 119, 317, 322, 323; 126/760, 767; 137/205; 141/35, 59, 65, 95, 198; 119/14.46

[56] References Cited

U.S. PATENT DOCUMENTS

| 1,910,830 | 5/1933 | Hapgood | 119/14.46 |
| 2,740,420 | 4/1956 | Hanks | 137/205 |
| 4,384,580 | 5/1983 | Leviton | 141/35 |

Primary Examiner—C. Fred Rosenbaum
Assistant Examiner—J. L. Kruter
Attorney, Agent, or Firm—Harris Zimmerman; Howard Cohen

[57] ABSTRACT

A fast response vacuum aspiration collection system includes a pair of sealed collection containers, one container having a significantly smaller volume. The larger container is connected to a fixed vacuum source, the smaller container is connected to a controlled, variable vacuum source, and the containers are connected together by an exchange line passing through a normally closed first pinch valve. A surgical probe line is connected to the exchange line, and extends through a normally closed second pinch valve to an aspirating surgical instrument. The controlled vacuum applied to the smaller container is conducted through the exchange line and the surgical line to the surgical instrument, with the small volume of the small container quickly assuming the vacuum level applied to that container. When the small container is filled, the second pinch valve is closed and the first pinch valve is opened, allowing the vacuum applied to the larger container quickly to withdraw fluid from the smaller container to the larger container.

14 Claims, 4 Drawing Figures

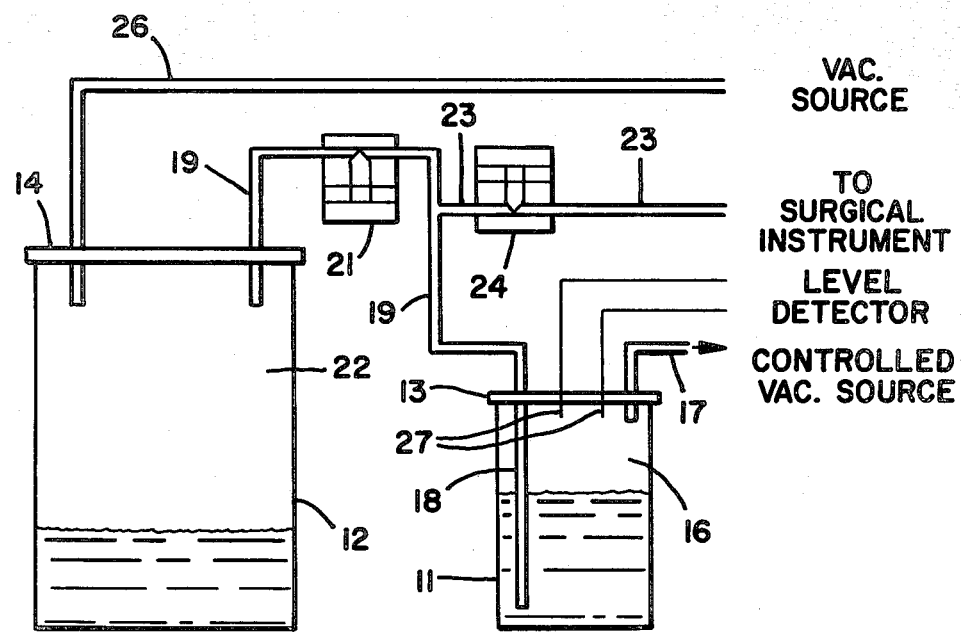
FIG _ 1
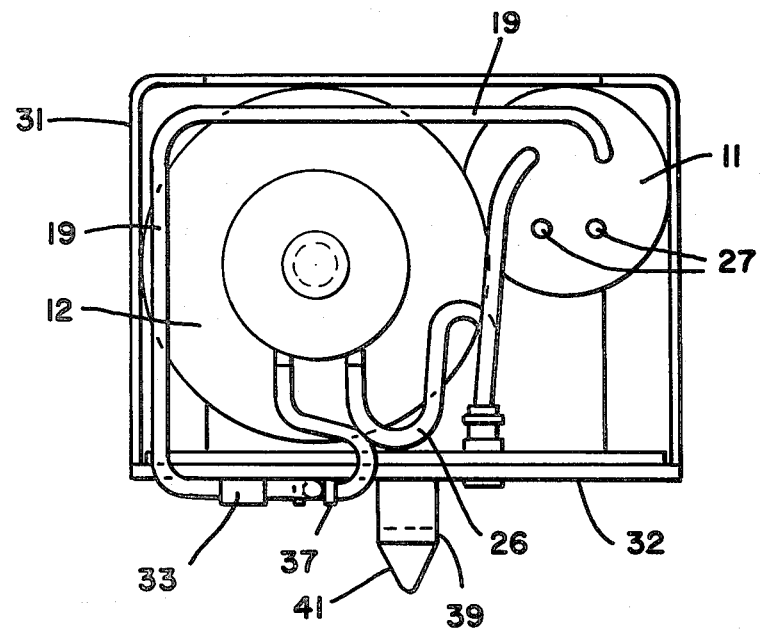
FIG _ 2

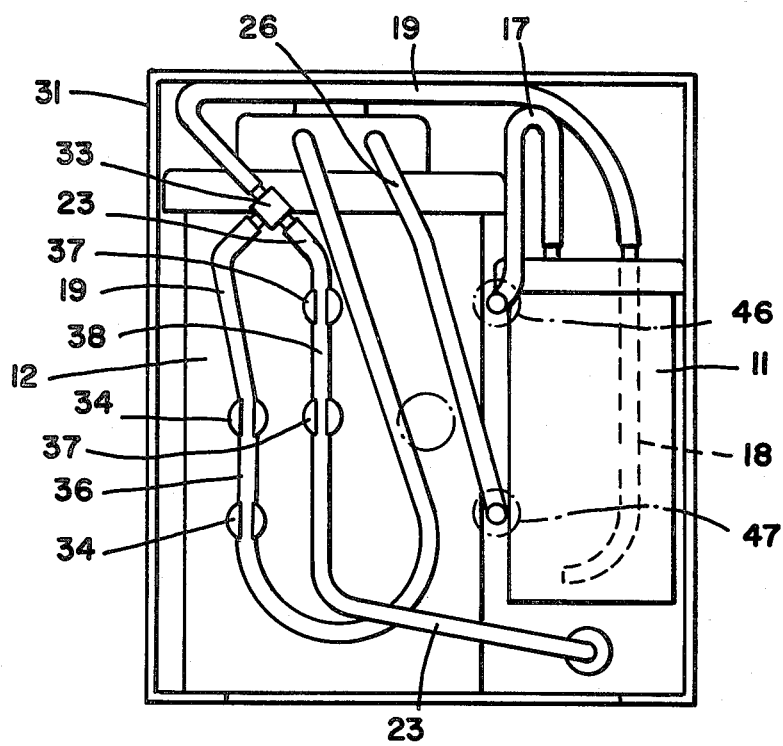
FIG _ 3
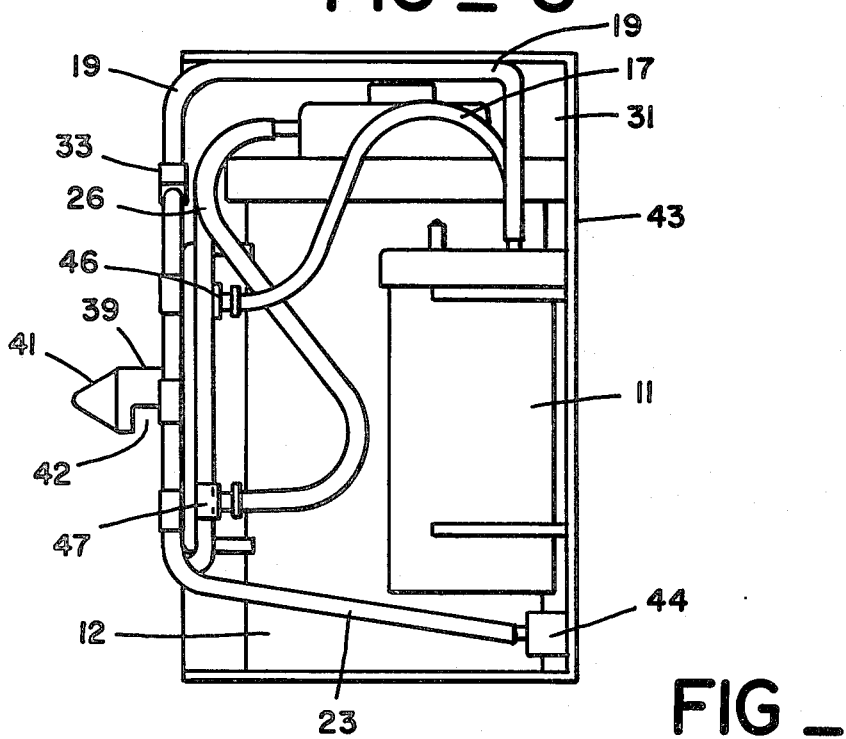
FIG _ 4

FAST RESPONSE VACUUM ASPIRATION COLLECTION SYSTEM

BACKGROUND OF THE INVENTION

In the field of surgery, it is well known to utilize vacuum aspiration for the removal of bodily fluids and irrigating fluids at the surgical site. In addition, in recent years vacuum aspiration has been used in conjunction with mechanical surgical cutters to enhance the effectiveness of the mechanical devices by drawing soft tissue into the mechanical cutting jaws by means of vacuum induction.

For example, in ophthalmological surgery, there have been developed devices for cutting and removing the fibrous vitreous material found within the eyeball. Such devices commonly employ a pair of concentric needles, the outer needle having an intake port adjacent to the distal end thereof. The inner needle is adapted to reciprocate within the outer needle, and includes a sharpened tip which reciprocates past the intake port of the outer needle. In such a device, tissue is drawn into the cutting port by means of vacuum aspiration applied through the needle assembly, the inner cutting tip shearing the tissue drawn into the port. The sheared tissue is then aspirated through the inner needle and delivered to a collection bottle.

Generally speaking, the aspirating vacuum applied to the port of the surgical instrument is created by a vacuum source which is applied to the collection bottle. Thus the vacuum applied to the collection bottle is delivered from that bottle through a flexible tubing connection to the surgical instrument.

A significant characteristic of such surgical instruments known in the prior art is that the rate at which tissue is excised and aspirated is primarily dependent upon the level of vacuum applied at the intake port of the instrument. If the vacuum level is too low, the tissue removal will proceed too slowly. However, if the vacuum level is too high, tissue will be drawn into the cutting instrument too rapidly. In this latter instance, tissue which should not be cut may be drawn into the instrument inadvertently, causing great damage to the eye. Thus it is clear that precise control of the level of vacuum applied to the mechanical cutter must be maintained at all times by the surgeon.

Generally speaking, such prior art surgical devices include a vacuum collection bottle which is sufficiently large to receive the maximum volume of effluvia (tissue, irrigation fluid, blood, etc.). Thus the collection bottle has a substantial volume which must be evacuated to the desired level to effect proper cutting of the surgical tool. However, the desired vacuum level changes from moment to moment in a surgical proceedure, in accordance with the nature of the tissue being cut, the proximity of the cutter to delicate tissues which must not be damaged, and the like. Moreover, whenever the surgical cutting tool is halted, even momentarily, the vacuum level within the collection bottle generally reverts to atmospheric pressure.

Due to the large volume of the vacuum collection bottle, a small but significant time period is required to reestablish the vacuum level within the collection bottle, or to alter the vacuum level to a new, desirable level. This time period, which may range from two to three and one-half seconds, requires the surgeon to proceed extremely slowly to avoid critical surgical errors. For example, when the surgeon is increasing the vacuum level to cut and remove denser or more fibrous tissue, the lag in response time of the vacuum aspiration system may cause the surgeon to believe that the new higher vacuum level is insufficient, when in fact the higher level has not yet been reached. The surgeon will then switch to an even higher vacuum level, in order to effect cutting of the heavier tissue. When these incremental increases in the vacuum level are finally delivered to the cutting port of the instrument, after a lag time of a few seconds, the vacuum level may be much too great and the resulting inrush of tissue into the cutting port may cause damage to surrounding tissues.

SUMMARY OF THE PRESENT INVENTION

The present invention generally comprises a fast response vacuum aspiration collection system for surgical use. A significant feature of the system is that the vacuum level applied to the cutting instrument may be selectively changed to a new level within a fraction of a second, while the system provides ample capacity for any contemplated surgery.

The collection system includes a pair of sealed collection containers, one container having a significantly smaller volume. The larger container is connected to a fixed vacuum source, and the smaller container is connected to a variable, controlled vacuum source. Both containers are connected together by an exchange line passing through a normally closed first pinch valve. A surgical probe line is connected to the exchange line, and extends through a normally closed second pinch valve to an aspirating surgical instrument. The controlled vacuum applied to the smaller container is conducted through the exchange line and the surgical line to the surgical instrument, with the small volume of the small container quickly assuming the vacuum level applied to that container. When the small container is filled, the second pinch valve is closed and the first pinch valve is opened, allowing the vacuum applied to the larger container quickly to withdraw fluid from the smaller container to the larger container.

BRIEF DESCRIPTION OF THE DRAWING

FIG. 1 is a schematic respresentation of the fast response vacuum aspiration collection system of the present invention.

FIG. 2 is a top view of the cassette embodiment of the fast response vacuum aspiration collection system of the present invention.

FIG. 3 is a front elevation of the cassette embodiment as shown in FIG. 2.

FIG. 4 is a side elevation of the cassette embodiment as shown in FIGS. 2 and 3.

DESCRIPTION OF THE PREFERRED EMBODIMENT

The present invention generally comprises a vacuum aspiration fluid collection system for use in conjunction with a surgical cutting device which employs vacuum aspiration as an integral part of the cutting operation. A most significant feature of the present invention is that it provides a large volume for retaining the aspirated surgical effluvia, while also providing virtually instantaneous changes in vacuum level as dictated by the surgeon employing the surgical cutter. With reference to FIG. 1, the invention includes a small primary container 11 and a significantly larger secondary container 12. In the preferred embodiment the container 11 has a volume of approximately 30 ml., while the larger container 12 has a volume of approximately 180 ml. Both containers 11 and 12 are provided with top closures 13 and 14, respectively, which seal their respective openings.

The primary container 11 has an interior chamber 16 which is sealed from atmospheric pressure by the top closure 13. The volume 16 is connected to a controlled vacuum source through a tubing line 17. Also connected to the closed volume 16 is an intake tube 18 which extends through the top closure 13 and substantially to the bottom of the container 11. The intake tube 18 is connected to an exchange tube 19. The other end of the tube 19 passes through a selectively controllable, normally closed pinch valve 21 and thence through the top closure 14 of the large container 12 to communicate with the interior volume 22 of the large container 12.

The invention also includes an aspiration line 23 which extends to a surgical cutting instrument as known in the prior art and described in the Background section herein. The aspiration line 23 comprises a flexible tube 20 which extends from the surgical instrument, through a selectively controlled, normally closed pinch valve 24, and thence to a connection with the tube 19 which interconnects the two containers. It should be noted that the connection of the line 23 and the line 19 is disposed between the pinch valve 21 and the connection to the container 11.

The interior chamber 22 of the secondary container 12 is connected by a tubing line 26 to a vacuum source. It should be noted that the vacuum source joined to line 26 is not the same controlled vacuum source which is connected to the primary container 11. The primary container 11 also includes a pair of electrodes 27 which extend through the top closure 13 and are disposed adjacent to the undersurface of the top closure 13. The electrodes 27 are connected to a level detection circuit which is completed by liquid within the volume 16 rising to the level of the electrodes 27 to conduct electricity therebetween. Such level detection devices are well known in the prior art.

In operation of the embodiment of FIG. 1, the line 17 is connected to a controlled vacuum source which is under the personal control of the surgeon. The line 23 is connected to the surgical cutting instrument which is also under the personal control of the surgeon. The controlled vacuum level is applied to the small volume 16, which quickly is evacuated to the level set by the control of the surgeon. For example, in use with a standard vitrectomy instrument, the vacuum level set by the surgeon through the line 17 will be applied at the cutting port of the surgical instrument within one-fifth of a second. This slight delay time is insignificant in controlling the vacuum at the cutting port, and overcomes the serious lag time problems known in prior art vacuum aspiration systems. The quick response time of the present invention is due to the small volume 16 which is quickly evacuated through line 17. It may be appreciated that the vacuum is applied from volume 16 through delivery line 18, tubing line 19, tubing line 23, selectively opened pinch valve 24, and thence to the surgical instrument. The pinch valve 21 remains closed so that the secondary container 12 is isolated from the primary container 11 and from the surgical aspiration line 23.

Due to the small volume 16 of the primary container 11, the container 11 may occasionally fill with fluids and solids aspirated from the surgical site. When the capacity of the container 11 is reached, the controlled vacuum source from line 17 is momentarily interrupted, the pinch valve 24 is allowed to assume its normally closed configuration, and the pinch valve 21 is momentarily opened. These actions permit the vacuum source communicated through tubing line 26 to apply a strong vacuum to the volume 22 of the secondary container 12. This vacuum is conducted through tubing line 19, through the open valve 21, and thence to the intake tube 18 within the primary container 11. The vaccum applied to the intake tube 18 withdraws all of the liquid and solid material from the container 11 and draws it into the secondary container 12. This removal of the contents of primary container 11 is effected within three or four seconds. Thereafter, the valve 21 is allowed to assume its normally closed disposition, and the primary container 11 is again in condition to receive the effluent from the surgical instrument.

It should be noted that during the short period in which the smaller container 11 is emptied into the larger container 12, the pinch valve 24 is maintained closed. Thus the vacuum aspiration to the surgical instrument is briefly interrupted while the exchange of effluent takes place. With the vacuum aspiration temporarily blocked from delivery to the surgical instrument, the instrument cannot cut and remove tissue. Thus no damage can be done to the eye tissue by inadvertent cutting during the exchange between the smaller and larger containers.

It may be appreciated that the exchange of effluent from smaller to larger containers may be initiated by a level detector device connected to the electrodes 27 in the smaller container 11. Such devices, which are well known in the prior art, may be used to actuate the pinch valve 21 while at the same time assuring deactuation of the pinch valve 24. The level detector control circuit may include a timer to restore operation of valve 24 and deactivate valve 21 after a brief time period sufficient to permit transfer of the effluent.

Alternatively, the transfer of effluent may be effected whenever the surgical instrument is turned off; i.e., when the instrument is switched from the cutting mode to the quiescent mode. In the latter mode, the valve 24 is closed to block the vacuum aspiration delivered to the surgical handpiece. Whenever valve 24 is closed, there is an opportunity to remove the contents of container 11 into container 12, merely by opening valve 21 whenever valve 24 is closed for more than a brief instant. This mode of emptying the container 11 whenever valve 24 is closed may be achieved through the use of electronic logic circuitry, pneumatic logic circuitry, or simply relay devices which actuate the valve 21 upon closure of the valve 24, and likewise deactuate valve 21 just prior to the actuation of valve 24.

Although the fast response vacuum aspiration collection system of the present invention appears extensive in the schematic representation of FIG. 1, the assembly may be formed in a compact structure convenient for use in conjunction with a surgical instrument control console. With reference to FIGS. 2, 3, and 4, a convenient embodiment of the invention includes a cassette holder 31 having the general configuration of a hollow rectangular prism. Within the cassette holder 31 there are supported the small container 11 and the much larger container 12. The cassette holder 31 includes a rear wall 32 formed integrally therewith. The tubing line 19 extends from the small container 11, extends across the upper portion of the cassette holder 31, and out through an opening in the rear wall 32 to join a T connector 33 mounted exteriorly on the rear wall 32. The remainder of the tubing line 19 extends from the T 33 downwardly and parallel to the rear wall 32 and through a pair of vertically spaced tubing brackets 34. The tubing section 36 located between the brackets 34 is adapted to be received in the pinch valve 21, as shown in FIG. 1. Likewise, the tubing line 23 extends downwardly from the T 33 and through a pair of tubing brackets 37. The tubing line 38 disposed between the brackets 37 is secured and disposed to be engaged by the pinch valve 24, as shown in FIG. 1.

Also joined to the rear wall 32 of the cassette 31 is a pilot pin 39. The pin 39 includes a tapered conical distal end 41 and a detent slot 42 extending chordally through a proximal portion thereof. The cassette 31 is adapted to be inserted in an appropriately formed recess in a control console for a surgical cutting instrument. The pilot pin 39 assures that the cassette 31 is appropriately positioned in the rescess in the control console, and the slot 42 engages a latch assembly which retains the cassette 31 in the recess. It may be appreciated that within the recess, the pinch valves 21 and 24 are disposed to engage the tubing sections 36 and 38, respectively, upon insertion of the cassette into the recess. Thus the need to extend the tubing lines through the appropriate pinch valves is alleviated, and thee is no opportunity for error in routing the tubing lines through the pinch valves.

The cassette holder 31 also includes a front wall 43. Extending through the lower portion of the front wall 43 is a connector receptacle 44 adapted to receive the vacuum aspiration line of a surgical cutting instrument. Within the cassette 31, the receptacle 44 is connected to the lower end of the tubing line 23.

The rear wall 32 of the cassette also includes a pair of connector receptacles 46 and 47. Receptacle 46 is connected to the lower end of tubing line 17, and receptacle 47 is connected to the lower end of tubing line 26. The receptacles 46 and 47 are positioned to be connected to appropriately formed fluid connectors within the recess of the surgical instrument control module, so that receptacle 46 is connected to the controlled vacuum source which is under the surgeon's control, and the receptacle 47 is connected to the vacuum source which is applied to the large container 22. Here again, the pilot pin 39 assures that the connectors 46 and 47 are properly aligned with the respective connectors within the control console of the surgical instrument.

It may be noted that the cassette holder 31 is preferably formed of molded plastic or the like, and may include window portions in the front wall 43 to facilitate visual monitoring of the liquid levels within the containers 11 and 12. Alternatively, the cassette holder 31 may be formed entirely of transparent plastic material. Appropriate openings may be made in the rear wall 32 so that the electrodes 27 extending upwardly from the container 11 may be connected to appropriate electrical connectors extending from the control console of the surgical instrument. Such connectors may extend from the control console so that insertion of the cassette holder 31 therein not only completes the vacuum connections, but also completes the electrical connection to the level detector electrodes.

I claim:

1. A fast response vacuum aspiration collection system, comprising an aspiration surgical instrument a pair of sealed collection containers, one container having a significantly smaller volume than the other, separate vacuum connected to each of said containers individually, an exchange line connected between said containers for open flow communication therebetween, a first valve interposed on said exchange line, an aspiration line connected to said aspirating surgical instrument at one end and connected to said exchange line at the other end, a second valve interposed on said aspirating line, said aspirating line joining said exchange line at a point located between said first valve and said one container.

2. The vacuum aspiration collection system of claim 1, wherein said vacuum means includes a controlled vacuum source connected to said one container to evacuate quickly said one container to the vacuum level of said controlled vacuum source, said controlled vacuum source adapted to be operated in conjunction with said surgical instrument.

3. The vacuum aspiration collection system of claim 2, wherein said vacuum means includes a constant vacuum source connected to said other container.

4. The vacuum aspiration collection system of claim 1, wherein said first and second valves are normally closed.

5. The vacuum aspiration collection system of claim 4, wherein said second valve is selectively actuable to connect said surgical instrument through said aspiration line and said exchange line to the vacuum level within said one container.

6. The vacuum aspiration collection system of claim 4, wherein said first valve is selectively actuable when said second valve is closed to connect the vacuum level in said other container through said exchange line to said one container to withdraw the contents of said one container into said other container.

7. The vacuum aspiration collection system of claim 4, wherein said first and second valves comprise pinch valves, and said exchange line and said aspiration line include flexible tubing portions extending through the respective valves.

8. The valve aspiration collection system of claim 1, wherein said exchange line includes an intake port disposed proximal to the lowest point in said one container to withdraw the entire liquid contents of said one container.

9. The vacuum aspiration collection system of claim 1, further including cassette holder means for supporting said one container and said other container.

10. The vacuum aspiration collection system of claim 9, further including a portion of said aspirating line extending exteriorly of said cassette holder means and disposed to engage a pinch valve comprising said second valve.

11. The vacuum aspiration collection system of claim 9, further including a portion of said exchange line extending exteriorly of said cassette holder means and disposed to engage a pinch valve comprising said first valve.

12. A fast response vacuum aspiration collection system, including an aspiration instrument first container means having a small volume and connected to controlled vacuum source means to be evacuated quickly to the vacuum level of said source, aspirating line means extending from said first container means to said aspirating instrument, said first container being disposed to capture and retain effluent from said instrument, second container means having a larger volume than the first container and connected to a second vacuum source, and exchange line means extending between said first and second containers to remove said effluent from said first container to said second container by vacuum induction.

13. The fast response vacuum aspiration collection system of claim 12, further including valve means for selectively blocking said aspirating line means and opening said exchange line means to effect said removal of said effluent from said first container to said second container.

14. The fast response vacuum aspiration collection system of claim 13, further including level detector means in said first container for actuating said valve means when said first container is filled to a predetermined level.

* * * * *